United States Patent
Yada et al.

(10) Patent No.: US 6,998,505 B2
(45) Date of Patent: Feb. 14, 2006

(54) PROCESS FOR PRODUCING (METH)ACRYLIC ACID COMPOUND

(75) Inventors: Shuhei Yada, Mie (JP); Hirochika Hosaka, Mie (JP); Kimikatsu Jinno, Mie (JP)

(73) Assignee: Mitsubishi Chemical Corporation, Tokyo (JP)

( * ) Notice: Subject to any disclaimer, the term of this patent is extended or adjusted under 35 U.S.C. 154(b) by 0 days.

(21) Appl. No.: 10/923,739

(22) Filed: Aug. 24, 2004

(65) Prior Publication Data

US 2005/0020852 A1    Jan. 27, 2005

Related U.S. Application Data

(63) Continuation of application No. PCT/JP03/02856, filed on Mar. 11, 2003.

(30) Foreign Application Priority Data

Mar. 11, 2002   (JP)   .............................. 2002-065532

(51) Int. Cl.
*C07C 51/16*   (2006.01)

(52) U.S. Cl. ................................... 562/545

(58) Field of Classification Search ................ 562/545
See application file for complete search history.

(56) References Cited

U.S. PATENT DOCUMENTS

4,365,087 A    12/1982    Kadowaki et al.
4,873,368 A    10/1989    Kadowaki et al.

FOREIGN PATENT DOCUMENTS

JP    58-015934    1/1983

*Primary Examiner*—Paul A Zucker
(74) *Attorney, Agent, or Firm*—Oblon, Spivak, McClelland, Maier & Neustadt, P.C.

(57) ABSTRACT

In a process for producing a (meth)acrylic acid compound by catalytic vapor phase oxidation, the (meth)acrylic acid compound is produced constantly and efficiently by preventing the change in the composition of the raw material mixed gas, the abnormal temperature increase in the oxidation reactor and the deterioration of the catalytic activity or the useful catalyst life. In the process for producing (meth) acrolein or (meth)acrylic acid by the catalytic vapor phase oxidation reaction of propylene, propane or isobutylene in the oxidation reactor, the temperature of the raw material mixed gas introduced to the oxidation reactor is maintained to be at least the dew point temperature of the raw material mixed gas.

3 Claims, 1 Drawing Sheet

PROCESS FOR PRODUCING ACRYLIC ACID
(TWO STEP OXIDATION PROCESS OF PROPYLENE)

PROCESS FOR PRODUCING ACRYLIC ACID
(TWO STEP OXIDATION PROCESS OF PROPYLENE)

*1: FIRST REACTOR
*2: SECOND REACTOR
*3: CONDENSATION COLUMN
*4: EXTRACTION COLUMN
*5: SOLVENT SEPARATION COLUMN
*6: ACETIC ACID SEPARATION COLUMN
*7: FRACTIONATING COLUMN
*8: SOLVENT RECOVERY COLUMN
*9: ACRYLIC ACID
*10: VENT
*11: WATER
*12: ACETIC ACID
*13: BY-PRODUCT

PROCESS FOR PRODUCING (METH)ACRYLIC ACID COMPOUND

This application is a continuation of PCT/JP03/02856, filed Mar. 11, 2003.

TECHNICAL FIELD

The present invention relates to a process for producing a (meth)acrylic acid compound, particularly to a process for producing (meth)acrolein or (meth)acrylic acid, which comprises reacting propylene, propane or isobutylene by catalytic vapor phase oxidation in an oxidation reactor, wherein deterioration of the catalytic activity or the useful catalyst life is prevented, thereby to produce the (meth)acrylic acid compound constantly and efficiently.

In the present invention, the (meth)acrylic acid compound means (meth)acrolein or (meth)acrylic acid, the (meth)acrolein means acrolein or methacrolein, and the (meth)acrylic acid means acrylic acid or methacrylic acid.

BACKGROUND ART

As a reaction for producing (meth)acrylic acid, there is a catalytic vapor phase oxidation method of propylene, propane or isobutylene. In the method for obtaining (meth)acrylic acid by catalytic vapor phase oxidation of propylene, propane or isobutylene, conditions for oxidation to (meth)acrolein and for oxidation to (meth)acrylic acid in the next step are different. Accordingly, there are a two step oxidation process in which the respective oxidation reactions are carried out by different catalysts or in separate reactors, and a process in which plural types of catalysts are packed in one reactor to carry out the oxidation reactions in the single reactor. In such a step for producing (meth)acrolein by catalytic vapor phase oxidation of propylene, propane or isobutylene by using a molecular oxygen and/or a step for producing (meth)acrylic acid by catalytic vapor phase oxidation of (meth)acrolein by using the molecular oxygen (hereinafter sometimes referred to as "process for producing a (meth)acrylic acid compound"), in order to adjust the catalytic activity and to prevent the formation of detonating gas, gaseous water (steam) is mixed to a gas comprising a combustible gas such as propylene and molecular oxygen to obtain a raw material mixed gas.

FIG. 1 is an example of a flow chart for producing acrylic acid by two step oxidation, wherein propylene with steam and air is oxidized in two steps via a first reactor and a second reactor having a molybdenum type catalyst or the like packed, to form an acrylic acid-containing gas. Such an acrylic acid-containing gas is contacted with water in a condensation column (quench column) to obtain an aqueous acrylic acid solution, which is extracted by adding a suitable extraction solvent, in an extraction column, whereupon the extraction solvent is separated in a solvent separation column. Then, acetic acid is separated in an acetic acid separation column to obtain a crude acrylic acid, and further, from the crude acrylic acid, byproducts are separated in a fractionating column to obtain a purified product of acrylic acid.

Further, in recent years, instead of the above solvent extraction method wherein recovery of acrylic acid from the aqueous acrylic acid solution is carried out by means of an extraction solvent, an azeotropic separation method is also employed wherein distillation is carried out by using water and an azeotropic solvent, so that from the top of an azeotropic separation column, an azeotropic mixture comprising water and the azeotropic solvent, is distilled, and from the bottom, acrylic acid is recovered.

In a case where methacrylic acid is produced by a catalytic vapor phase oxidation method, isobutylene is subjected to vapor phase oxidation. In the case of the two step oxidation method, isobutylene is oxidized to methacrylic acid via methacrolein.

In the process for producing a (meth)acrylic acid compound, the composition of a raw material mixed gas comprising a combustible gas such as propylene, molecular oxygen and gaseous water, may change to decrease the yield of the desired product, or the temperature of the catalyst layers may abruptly increase to form hot spots, thus leading to deterioration in the performance of the catalyst or to a damage of the production apparatus.

JP-A-5-229984 discloses a method for producing acrylic acid by oxidizing acrolein, wherein the raw material acrolein is preheated to increase the selectivity for acrylic acid. Further, JP-A-2000-53610 discloses the ratio in a raw material mixed gas and the raw material mixed gas temperature at the reactor inlet to improve the yield of acrylic acid. However, such methods had a problem of deterioration of the catalytic activity or the useful life of the catalyst.

It is an object of the present invention to provide a process for producing (meth)acrolein or (meth)acrylic acid, which comprises reacting propylene, propane or isobutylene by catalytic vapor phase oxidation in an oxidation reactor, wherein the change of the composition of the raw material mixed gas, the abnormal temperature increase in the oxidation reactor, and the deterioration of the catalytic activity or the useful catalyst life is prevented to produce the (meth)acrylic acid compound constantly and efficiently.

DISCLOSURE OF THE INVENTION

The process for producing a (meth)acrylic acid compound of the present invention is a process for producing a (meth)acrylic acid compound, which comprises reacting a raw material mixed gas by catalytic vapor phase oxidation in an oxidation reactor to produce (meth)acrolein or (meth)acrylic acid, characterized in that the temperature of the raw material mixed gas introduced into the oxidation reactor is maintained to be at least the dew point temperature of the raw material mixed gas.

Heretofore, water in liquid state formed by condensation of gaseous water contained in the raw material mixed gas, is in contact with a catalyst, whereby the activity or the useful life of the catalyst is deteriorated. Further, by the formation of such liquid state water, the composition of the raw material mixed gas supplied, will be changed, whereby hot spots will be formed, thus leading to problems such as deterioration of the yield of the desired product, deterioration of the catalytic performance, and damage of the production apparatus, due to the abnormal temperature increase.

In the present invention, by maintaining the temperature of the raw material mixed gas introduced into the oxidation reactor to be at least the dew point temperature of the raw material mixed gas, the raw material mixed gas not containing liquid state water is introduced into the oxidation reactor, whereby the above problems caused by the liquid state water in the raw material mixed gas are solved.

In the present invention, it is preferred that the conduit for supplying the raw material mixed gas from a raw material mixer to the oxidation reactor is heated and/or kept warm, to control the temperature of the raw material mixed gas.

Further, the temperature of the raw material mixed gas introduced into the oxidation reactor is preferably at most 260° C.

MODE FOR CARRYING OUT THE INVENTION

Figure 1:
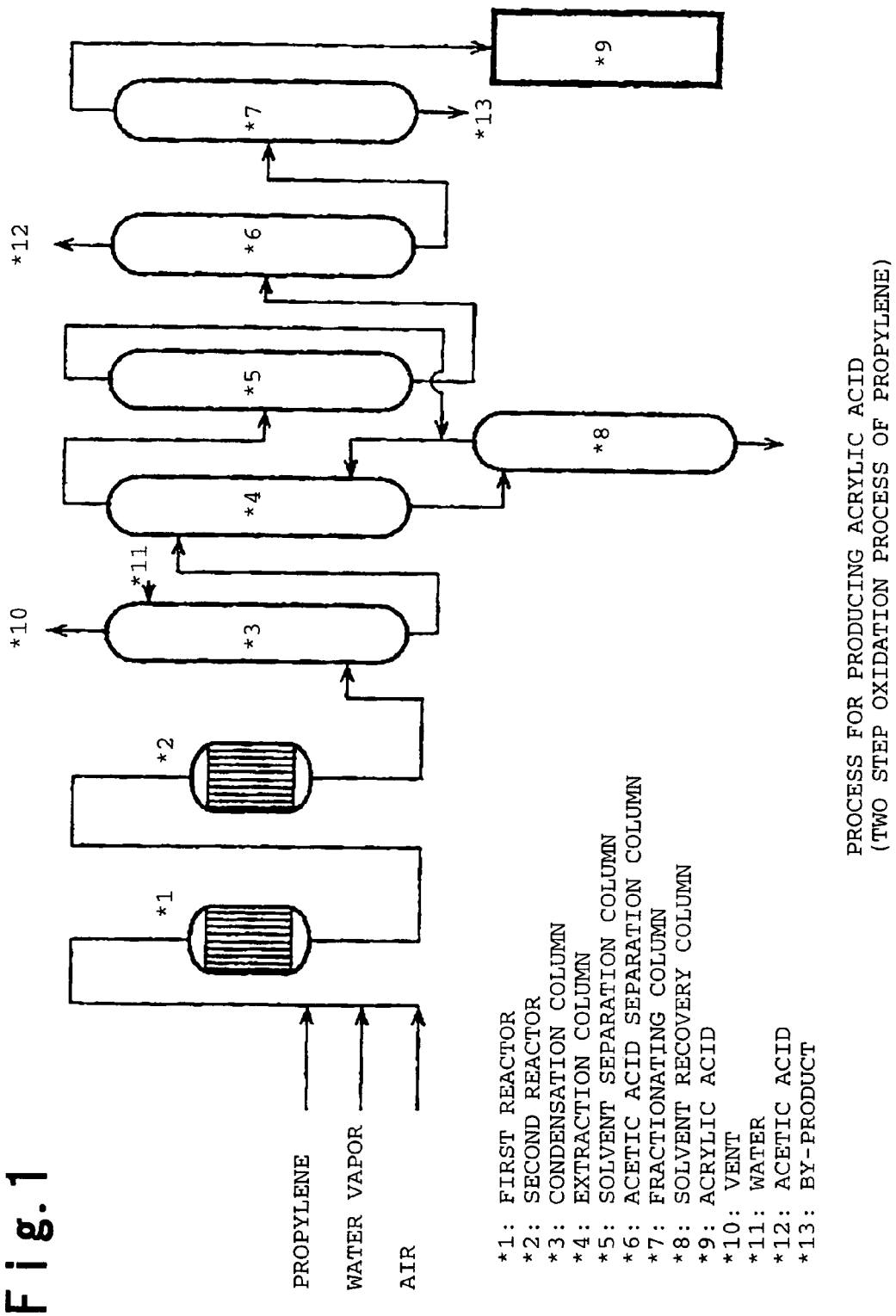
FIG. 1: A flow sheet which shows one example of the production process of acrylic acid.

Now, a mode for carrying out of the process for producing a (meth)acrylic acid compound of the present invention will be described in detail.

The process of the present invention may be suitably applied particularly to a process for producing (meth)acrolein or a (meth)acrylic acid compound by oxidation of propylene, propane or isobutylene with a molecular oxygen-containing gas by using a multi-tubular reactor, or a process for producing (meth)acrylic acid by oxidation of (meth)acrolein with a molecular oxygen-containing gas by using a multi-tubular reactor.

As mentioned above, propylene, propane or isobutylene is oxidized in two steps, in which (meth)acrylic acid is produced via (meth)acrolein. Accordingly, the production of (meth)acrylic acid from propylene, propane or isobutylene is carried out by using two multi-tubular reactors, as shown in FIG. 1. The reaction may be carried out by packing different catalysts in the respective reactors, or, a process for producing (meth)acrylic acid may be employed in which the shell side of a single reactor is divided into at least 2 reaction compartments by a middle-tube plate and different catalysts are packed in the respective compartments. Thus, the present invention may be applied to either process.

The catalyst to be used for producing (meth)acrylic acid is not particularly limited, but a molybdenum type multi-component composite metal oxide which is commonly used, is preferred.

To the oxidation reactor such as a multi-tubular reactor, a raw material mixed gas is introduced, which comprises propylene, propane or isobutylene, steam and molecular oxygen and which is adjusted by a component inert to a reaction such as nitrogen or carbon dioxide. Such a raw material mixed gas is prepared by mixing a raw material such as propylene, water, air, etc. in a raw material mixer provided at a stage prior to the oxidation reactor.

In the present invention, for example, the conduit for supplying the raw material mixed gas from such a raw material mixer to the oxidation reactor, is covered with a heat insulating material, or kept warm by a trace using a high temperature fluid such as steam or hot water, or the raw material mixed gas to be supplied to the oxidation reactor is heated by a heater provided between the raw material mixer and the oxidation reactor. Thus, the temperature of the raw material mixed gas introduced into the oxidation reactor is maintained to be at least the dew point temperature of the raw material mixed gas.

In order to maintain the temperature of the raw material mixed gas introduced to the oxidation reactor to be at least the dew point temperature by keeping warm and/or heating in such a manner, the following method may, for example, be employed. A thermometer and a pressure gauge are provided at the upstream side of the inlet of the oxidation reactor, and the dew point of the raw material mixed gas is obtained by calculation from the composition and the pressure of the raw material mixed gas. The temperatures of the respective raw material components supplied to the raw material mixed gas and/or the heating temperature by the heater (the outlet temperature of the heater) may be controlled so that the value measured by the thermometer provided at the upstream side of the inlet of the oxidation reactor will be at least the dew point temperature calculated as mentioned above.

By thus maintaining the temperature of the raw material mixed gas introduced to the oxidation reactor to be at least the dew point temperature, the composition of the raw material mixed gas will not deviate from the set value, and the raw material mixed gas of the prescribed composition will be introduced to the catalyst layers of the oxidation reactor. Further, the temperature increase to form hot spots of the catalyst layers is also prevented, whereby it becomes possible to obtain the desired product in high yield.

Now, an example of the method for calculating the dew point of the raw material mixed gas is shown. For example, if propylene at 45° C.: 10 vol %, air at 100° C.: 75 vol %, a heated water vapor (steam) at 132° C.: 10 vol %, and nitrogen at 20° C.: 5 vol % are mixed to obtain a raw material mixed gas having a pressure of P=170 kPa, the dew point t will be 56.6° C. by an Antoine formula of $\log_{10} P$ [kPa]=7.074−1657/(227.0+t(° C.)).

In the present invention, the temperature of the raw material mixed gas to be introduced to the oxidation reactor, which is maintained by keeping warm and/or heating the raw material mixed gas supplied from the raw material mixer to the oxidation reactor, may vary depending on the dew point of the raw material mixed gas, namely, the composition or the pressure. However, in a usual case, the lower limit of such temperature is preferably 60° C., more preferably 80° C. Further, the upper limit temperature of the raw material mixed gas is preferably 260° C., more preferably 240° C., furthermore preferably 220° C. Particularly, the temperature of the raw material mixed gas to be introduced to the oxidation reactor is preferably a temperature higher by from 5 to 25° C. than the dew point temperature of the raw material mixed gas.

By selecting the above preferred temperature range, abnormal deterioration of the catalytic activity of the catalysts in the oxidation reactor can be prevented, and the abnormal increase of the temperature can be prevented, whereby it is possible to produce a (meth)acrylic acid compound constantly and efficiently.

Further, in the present invention, it is possible to produce a (meth)acrylic acid compound in accordance with a usual manner, except that the temperature of the raw material mixed gas to be introduced to the oxidation reactor is maintained to be at least the dew point temperature of the raw material mixed gas by keeping warm and/or heating the raw material mixed gas supplied from the raw material mixer to the oxidation reactor. For example, usual conditions may be employed with respect to the composition of the raw material mixed gas or the reaction conditions in the oxidation reactor.

In general, the composition of the raw material mixed gas, may properly be set within such a range that the material such as propylene, propane or isobutylene is from 5 to 13 vol %, air is from 37 to 87 vol %, steam is from 3 to 26 vol %, and nitrogen is from 0 to 55 vol %.

EXAMPLES

Now, the present invention will be described in further detail with reference to Examples and Comparative Examples.

Example 1

To carry out the oxidation reaction of propylene, as the earlier stage catalyst, a catalyst powder having a composition of $Mo_{12}Bi_5Ni_3Co_2Fe_{0.4}Na_{0.2}B_{0.4}K_{0.1}Si_{24}O_x$ (the composition x of oxygen is a value defined by the oxidation conditions of the respective metals) was produced. The catalyst powder was formed into a ring catalyst having an outer diameter of 5 mm, an inner diameter of 2 mm and a height of 4 mm. As a reactor, a multi-tubular reactor was used, which had stainless steel reaction tubes with a length of 3.5 m, an inner diameter of 24 mm and an outer diameter of 28 mm, and which had a shell inner diameter of 100 mm. As a heating medium, a molten-salt Niter of a nitrate mixture was used, and it was supplied from the top of the reactor. As the reaction temperature, the temperature of the Niter as the heating medium supplied to the reactor was adopted.

1.5 Liters of the earlier stage ring catalyst was packed in the respective reaction tubes, and the raw material mixed gas was supplied at 170 kPa (kilopascal) from the top of the reactor.

As the raw material mixed gas, a mixture obtained by mixing propylene, air, steam and nitrogen in proportions of 10 vol %, 75 vol %, 10 vol % and 5 vol %, respectively, was used. The dew point of this raw material mixed gas was 56.6° C.

The conduit between the mixer for the raw material mixed gas and the reactor was traced by low-pressure steam and covered with a heat insulating material to keep it warm. Further, a thermocouple and a pressure gauge were provided at the inlet portion of the reactor, and the dew point of the raw material mixed gas was calculated and monitored all the time by using a computer. At the same time, by means of a heater provided between the mixer and the reactor, the temperature of the raw material mixed gas at the inlet of the reactor was controlled to be at least the dew point temperature by a temperature regulator, and the operation was carried out so that the temperature of the raw material mixed gas measured by the thermocouple provided at the inlet portion of the reactor was constant at 80° C.

Further, the temperature distribution was measured by inserting in the reaction tube of the reactor, a thermometer having ten measurement points in the tube axis direction.

The temperature of the heating medium was set at 330° C., and the operation was carried out for one week, whereby the conversion of propylene was 97%, the yield of acrolein was 92%, and the maximum temperature in the reaction catalyst layers was 400° C. The operation was carried out for one month from the initiation of the operation while the temperature of the heating medium was maintained to be 330° C., whereby upon expiration of the one month, the conversion of propylene was 96.8%, the yield of acrolein was 91.9%, and the maximum temperature in the reaction catalyst layers was 385° C.

During the period, the indicated temperature of the thermocouple provided at the inlet of the reactor was constant at 80° C. Further, the composition of the raw material mixed gas at the inlet of the reactor was analyzed by gas chromatography and the measured values were equal to the set values.

Comparative Example 1

The operation was carried out in the same manner as in Example 1 except that the steam for the trace was stopped, the heat insulating material was removed, and the temperature control of the heater was cancelled.

The temperature of the heating medium was set at 330° C., and the operation was carried out for a week, whereby the conversion of propylene was 97%, the yield of acrolein was 91%, and the hot spot temperature of the reaction catalyst layers was 410° C. While the temperature of the heating medium was maintained to be 330° C., the operation was carried out for one month from the initiation of the operation, whereby the conversion of propylene was 95.8%, the yield of acrolein was 89.5%, and the hot spot temperature of the reaction catalyst layers was 400° C.

During the period, the indicated temperature of the thermocouple provided at the inlet of the reactor was from 40 to 42° C. Further, the composition of the raw material mixed gas at the inlet of the reactor was analyzed by the gas chromatography, whereby propylene was 10.6 vol %, air was 74.4 vol %, water was 4.4 vol %, and nitrogen was 10.6 vol %.

The operation was suspended, and the apparatus was dismantled for inspection, whereby residual water was observed in the conduit.

Industrial Applicability

According to the present invention, in the process for producing (meth)acrolein or (meth)acrylic acid by the catalytic vapor phase oxidation reaction of propylene, propane or isobutylene in a oxidation reactor, it is possible to produce the (meth)acrylic acid compound constantly and efficiently by preventing the change of the composition of the raw material mixed gas, the abnormal temperature increase in the oxidation reactor and the deterioration of the catalytic activity or the useful catalyst life.

The entire disclosure of Japanese Patent Application No. 2002-65532 filed on Mar. 11, 2002 including specification, claims, drawings and summary is incorporated herein by reference in its entirety.

What is claimed is:

1. A process for producing a (meth)acrylic acid compound, which comprises reacting a raw material mixed gas by catalytic vapor phase oxidation in an oxidation reactor to produce (meth)acrolein or (meth)acrylic acid, characterized in that the temperature of the raw material mixed gas introduced to the oxidation reactor is maintained to be at least the dew point temperature of the raw material mixed gas, wherein the temperature of the raw material mixed gas introduced to the oxidation reactor is maintained to be higher by from 5 to 25° C. than the dew point temperature of the raw material mixed gas.

2. A process for producing a (meth)acrylic acid compound, which comprises reacting a raw material mixed gas by catalytic vapor phase oxidation in an oxidation reactor to produce (meth)acrolein or (meth)acrylic acid, characterized in that the temperature of the raw material mixed gas introduced to the oxidation reactor is maintained to be at least the dew point temperature of the raw material mixed gas, wherein the at least the dew point temperature of the raw material mixed gas is maintained by providing a thermometer and a pressure gauge at the upstream side of the inlet of the oxidation reactor, and the dew point of the raw material mixed gas is obtained by calculation from the composition and the pressure of the raw material mixed gas.

3. The process for producing a (meth)acrylic acid compound according to claim 2, wherein the temperatures of the respective raw material components supplied to the raw material mixed gas and/or the heating temperature by the heater is controlled so that the value measured by said thermometer is at least the dew point temperature so calculated.

* * * * *